United States Patent
Trenholm et al.

(10) Patent No.: US 11,449,757 B2
(45) Date of Patent: Sep. 20, 2022

(54) NEURAL NETWORK SYSTEM FOR NON-DESTRUCTIVE OPTICAL COHERENCE TOMOGRAPHY

(71) Applicant: SIGHTLINE INNOVATION INC., Toronto (CA)

(72) Inventors: Wallace Trenholm, Toronto (CA); Mark Alexiuk, Winnipeg (CA); Hieu Dang, Winnipeg (CA); Siavash Malektaji, Winnipeg (CA); Kamal Darchinimaragheh, Winnipeg (CA)

( * ) Notice: Subject to any disclaimer, the term of this patent is extended or adjusted under 35 U.S.C. 154(b) by 480 days.

(21) Appl. No.: 16/613,843

(22) PCT Filed: May 16, 2018

(86) PCT No.: PCT/CA2018/050579
§ 371 (c)(1),
(2) Date: Nov. 15, 2019

(87) PCT Pub. No.: WO2018/209438
PCT Pub. Date: Nov. 22, 2018

(65) Prior Publication Data
US 2020/0167656 A1   May 28, 2020

Related U.S. Application Data

(60) Provisional application No. 62/506,696, filed on May 16, 2017.

(51) Int. Cl.
*G06K 9/00* (2022.01)
*G06N 3/08* (2006.01)
(Continued)

(52) U.S. Cl.
CPC ............ *G06N 3/084* (2013.01); *G06F 17/18* (2013.01); *G06N 3/0454* (2013.01); *G06N 20/20* (2019.01);
(Continued)

(58) Field of Classification Search
CPC ............ G01B 9/02091; G01B 9/02063; G01B 11/2441; G01B 9/02083; G01B 9/02028;
(Continued)

(56) References Cited

U.S. PATENT DOCUMENTS

| 8,223,143 B2 | 7/2012 | Dastmalchi |
| 8,711,364 B2 | 4/2014 | Brennan |

(Continued)

OTHER PUBLICATIONS

Liu, Automated macular pathology diagnosis in retinal OCT images using multi-scale spatial pyramid and local binary patterns in texture and shape encoding, Jun. 2011, Elsevier (Year: 2011).*
(Continued)

*Primary Examiner* — Alex Kok S Liew
(74) *Attorney, Agent, or Firm* — Bhole IP Law; Anil Bhole; Marc Lampert

(57) ABSTRACT

A system and method for non-destructive optical coherence tomography (OCT) is provided. The system includes: an input interface for receiving OCT data including at least a C-scan; a processing unit executable to detect a feature on a surface or subsurface of the object, trained using a training set and configured to: separate the C-scan into A-scans; using a neural network, successively analyze each A-scan to detect the presence of an A-scan feature associated with the object; separate the C-scan into B-scans; segment each of the B-scans to determine thresholds associated with the object; using a neural network, successively analyze each segmented B-scan to detect the presence of an B-scan feature associated with the object; convert the C-scan to one or more two-dimensional representations; and using a neural network, detect the presence of an C-scan feature associated with the object.

20 Claims, 14 Drawing Sheets

(51) Int. Cl.
  *G06T 7/11* (2017.01)
  *G06N 20/20* (2019.01)
  *G06F 17/18* (2006.01)
  *G06N 3/04* (2006.01)
  *G06T 7/00* (2017.01)

(52) U.S. Cl.
  CPC .............. *G06T 7/0012* (2013.01); *G06T 7/11* (2017.01); *G06T 2207/10101* (2013.01); *G06T 2207/20081* (2013.01); *G06T 2207/20084* (2013.01)

(58) Field of Classification Search
  CPC ............. G01B 9/02035; G06N 3/0454; G06N 3/0445; G06N 3/084; G06N 3/0472; G06N 3/08; G06N 20/20; G06N 3/04; G06N 3/0427; G06N 3/0481; G06N 3/063; G06N 3/082; G06N 5/003; G06N 7/005
  See application file for complete search history.

(56) References Cited

U.S. PATENT DOCUMENTS

2002/0186818 A1* 12/2002 Arnaud .................. G06Q 30/02
  378/165
2015/0062590 A1   3/2015 Bagherinia

OTHER PUBLICATIONS

Kang, Deep learning-based autonomous underground cavity detection using 3D GPR, 2018, 9th European Workshop on Structural Health Monitoring Jul. 10-13, 2018, Manchester, United Kingdom (Year: 2018).*
Li, "Multi-Instance Multi-Scale CNN for Medical Image Classification," 2019, Springer (Year: 2019).*
International Search Report for PCT/CA2018/050579, Canadian Intellectual Property Office, dated Sep. 6, 2018.
Written Opinion for PCT/CA2018/050579, Canadian Intellectual Property Office, dated Sep. 6, 2018.

* cited by examiner

NEURAL NETWORK SYSTEM FOR NON-DESTRUCTIVE OPTICAL COHERENCE TOMOGRAPHY

TECHNICAL FIELD

The following relates generally to imaging interpretation and more specifically to a neural network system for non-destructive optical coherence tomography.

BACKGROUND

In many applications, imaging can be used to garner information about a particular object; particularly aspects about its surface or subsurface. One such imaging technique is tomography. A device practicing tomography images an object by sections or sectioning, through the use of a penetrating wave. Conventionally, tomography can be used for various applications; for example, radiology, biology, materials science, manufacturing, or the like. Some types of tomography include, for example, optical coherence tomography, x-ray tomography, positron emission tomography, optical projection tomography, or the like.

Conventionally, the above types of tomography, and especially optical coherence tomography, produce detailed imaging; however, such imaging can elicit a lot of data which can make feature extraction difficult and laborious.

SUMMARY

In an aspect, there is provided a method and neural network system for non-destructive optical coherence tomography (OCT), the system comprising: an input interface for receiving OCT data of an object, the OCT data comprising at least a C-scan; a processing unit executable to detect a feature on a surface or subsurface of the object via a data science module, the data science module trained using a training set and configured to: separate the C-scan into A-scans; using a neural network, successively analyze each A-scan to detect the presence of an A-scan feature associated with the object; separate the C-scan into B-scans; segment each of the B-scans to determine thresholds associated with the object; using a neural network, successively analyze each segmented B-scan to detect the presence of an B-scan feature associated with the object; convert the C-scan to one or more two-dimensional representations; and using a neural network, detect the presence of an C-scan feature associated with the object; and an output interface for outputting the determinations of the processing unit.

These and other aspects are contemplated and described herein. It will be appreciated that the foregoing summary sets out representative aspects of systems and methods to assist skilled readers in understanding the following detailed description.

BRIEF DESCRIPTION OF THE DRAWINGS

The features of the invention will become more apparent in the following detailed description in which reference is made to the appended drawings wherein.

DETAILED DESCRIPTION

Figure 1:
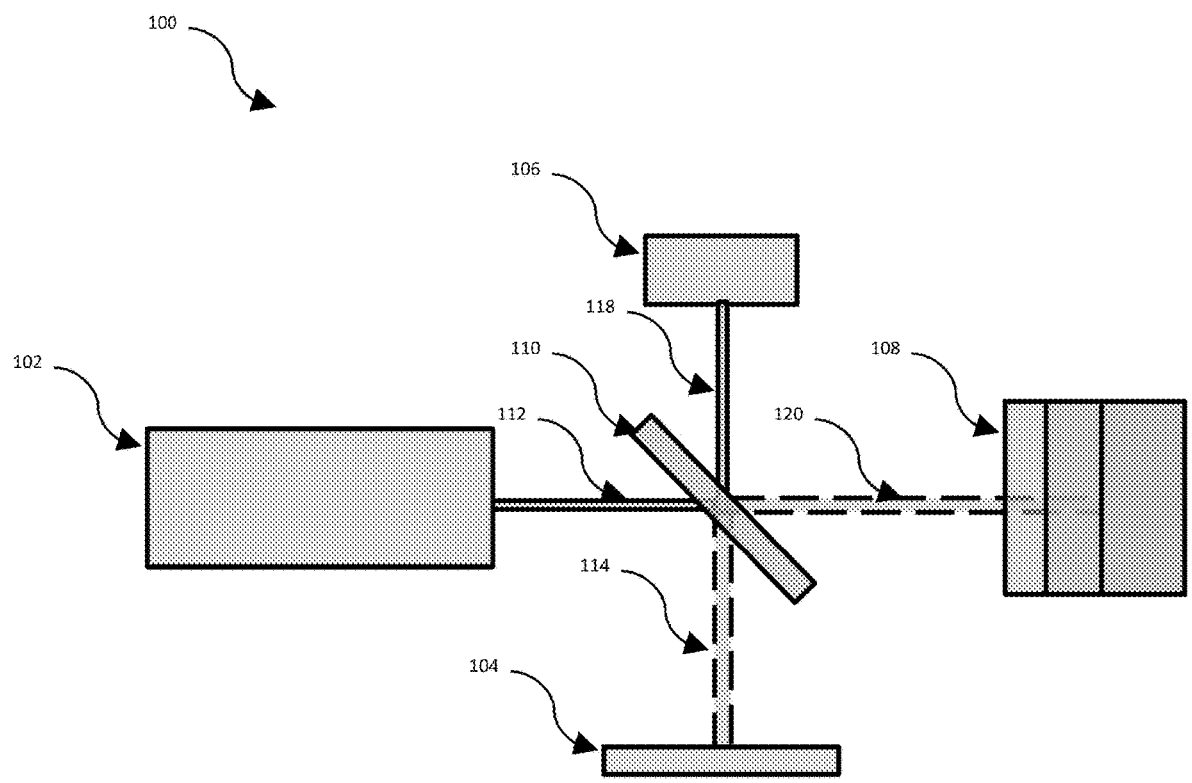
FIG. 1 is schematic diagram of an optical coherence tomography (OCT) system, according to an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to imaging interpretation and more specifically to a neural network system for non-destructive optical coherence tomography.

Optical coherence tomography (OCT), and particularly non-destructive OCT, is a technique for imaging in two or three-dimensions. OCT can provide a relatively high resolution, potentially up to few micrometers, and can have relatively deep penetration, potentially up to a few millimeters, in a scattering media.

OCT techniques can use back-scattered light from an object to generate information about that object; for example, generating a three-dimensional representation of that object when different regions of the object are imaged.

FIG. 1 illustrates a schematic diagram of an OCT system 100, according to an embodiment. The OCT system 100 includes an optical source 102, a reflective element 104 (for example, a mirror), a beam splitter 110, and a detector 106. The diagram shows an object 108 with three layers of depth. The optical source 102 produces an originating optical beam 112 that is directed towards the beam splitter 110. The beam splitter 110 divides the originating beam 112 and directs one derivative beam 114 towards the reflective element 104 and another derivative beam, referred to herein as the sample beam 120, towards the object to be scanned 108. Both derivative beams 114, 120 are directed back to the beam splitter 110, and then directed as a resultant beam 118 to the detector 106. In some cases, one or more secondary mirrors (not shown) can be provided to reflect the sample beam 120 onto the object 108; particularly in circumstances where the object 108 cannot be physically placed in the line of sight of the sample beam 120 due to physical constraints.

OCT systems 100 generally use different localization techniques to obtain information in the axial direction, along the axis of the originating optical beam 112 (z-axis), and obtain information in the transverse direction, along a plane perpendicular to the axis of the originating beam 112 (x-y axes). Information gained from the axial direction can be determined by estimating the time delay of the optical beam reflected from structures or layers associated with the object 108. OCT systems 100 can indirectly measure the time delay of the optical beam using low-coherence interferometry.

Typically OCT systems that employ low-coherence interferometers can use an optical source 102 that produces an optical beam 112 with a broad optical bandwidth. The originating optical beam 112 coming out of the source 102 can be split by the beam splitter 110 into two derivative beams (or paths). The first derivative beam 114 can be referred to as the reference beam (or arm) and the second derivative beam 120 can be referred to as the sample beam (or arm) of the interferometer. Each derivative beam 114, 120 is reflected back and combined at the detector 106.

The detector 106 can detect an interference effect (fast modulations in intensity) if the time travelled by each derivative beam in the reference arm and sample arm are approximately equal; whereby "equal" generally means a difference of less than a 'coherence length.' Thus, the presence of interference serves as a relative measure of distance travelled by light.

For OCT, the reference arm can be scanned in a controlled manner, and the reference beam 114 can be recorded at the detector 106. An interference pattern can be detected when the mirror 104 is nearly equidistant to one of the reflecting structures or layers associated with the object 108. The detected distance between two locations where the interference occurs corresponds to the optical distance between two reflecting structures or layers of the object in the path of the beam. Advantageously, even though the optical beam can pass through different structures or layers in the object, OCT can be used to separate out the amount of reflections from individual structures or layers in the path of the optical beam.

With respect to obtaining information in the transverse direction, the originating beam 112 can be focused on a small area of the object 108, potentially on the order of a few microns, and scanned over a region of the object.

In another embodiment of an OCT system, Fourier-domain can be used as a potentially efficient approach for implementation of low-coherence interferometry. Instead of recording intensity at different locations of the reference reflective element 104, intensity can be detected as a function of wavelengths or frequencies of the optical beam 112. In this case, intensity modulations, as a function of frequency, are referred to as spectral interference. Whereby, a rate of variation of intensity over different frequencies can be indicative of a location of the different reflecting structures or layers associated with the object. A Fourier transform of spectral interference information can then be used to provide information similar to information obtained from moving the optical beam, as described above.

In an embodiment of an OCT system, spectral interference can be obtained using either, or both, of spectral-domain techniques and swept-source techniques. With the spectral-domain technique, the optical beam can be split into different wavelengths and detected by the detector 106 using spectrometry. In the swept-source technique, the optical beam produced by the optical source 102 can sweep through a range of optical wavelengths, with a temporal output of the detector 106 being converted to spectral interference.

Advantageously, employing Fourier-domain can allow for faster imaging because back reflections from the object can be measured simultaneously.

The resolution of the axial and transverse information can be considered independent. Axial resolution is generally related to the bandwidth, or the coherence-length, of the originating beam 112. In the case of a Gaussian spectrum, the axial resolution ($I_c$) can be: $I_c = 0.44 * I^2 / DI$, where I is the central wavelength of the optical beam and DI is the bandwidth of the originating beam. In other cases, for spectrum of arbitrary shape, the axial spread function can be estimated as required.

The depth of the topography imaging for an OCT system is typically limited by the depth of penetration of the optical beam into the object 108, and in some cases, by the finite number of pixels and optical resolution of the spectrometer associated with the detector 106. Generally, total length or depth after Fourier transform is limited by the sampling rate of the spectral information, and is typically governed by the Nyquist theorem. A total bandwidth (DI) sampled by N pixels generates a wavelength sampling rate of dl=DI/N. This can be converted to the frequency domain as $dn=c*DI/l^2$. The Nyquist theorem indicates that a maximum time delay can be $t_{max}=1/2*dn$, and maximum depth can be $I_{max}=c*t_{max}$. A combination of these functions gives a maximum imaging depth of $I_{max}=1/2*(l^2/(DI/N))$.

With OCT systems, sensitivity is generally dependent on the distance, and thus delay, of reflection. Sensitivity is generally related to depth by: $R(z)=\sin(p*z)/(p*z)*\exp(-z^2/(w*p))$. Where w depends on the optical resolution of spectrometer associated with the detector 106. The first term related to the finite pixels in the spectrometer and the second term related to the finite optical resolution of the spectrometer.

When implementing the OCT system 100, reflected sample and reference optical beams that are outside of the coherence length will theoretically not interfere. This reflectivity profile, called an A-scan, contains information about the spatial dimensions, layers and location of structures within the object 108 of varying axial-depths; where the 'axial' direction is along the axis of the optical beam path. A cross-sectional tomograph, called a B-scan, may be achieved by laterally combining a series of adjacent A-scans along an axis orthogonal to the axial direction. A B-scan can be considered a slice of the volume being imaged. One can then further combine a series of adjacent B-scans to form a volume which is called a C-scan. Once an imaging volume has been so composed, a tomograph, or slice, can be computed along any arbitrary plane in the volume A-scans represent an intensity profile of the object, and its values (or profile) characterize reflectance of the way the optical beam penetrates the surface of the object. Thus, such scans can be used to characterize the material from the surface of the object to some depth, at an approximately single region of the object 108. B-scans can be used to provide material characterization from the surface of the object 108 to some depth, across a contour on the surface of the object 108.

Figure 2:
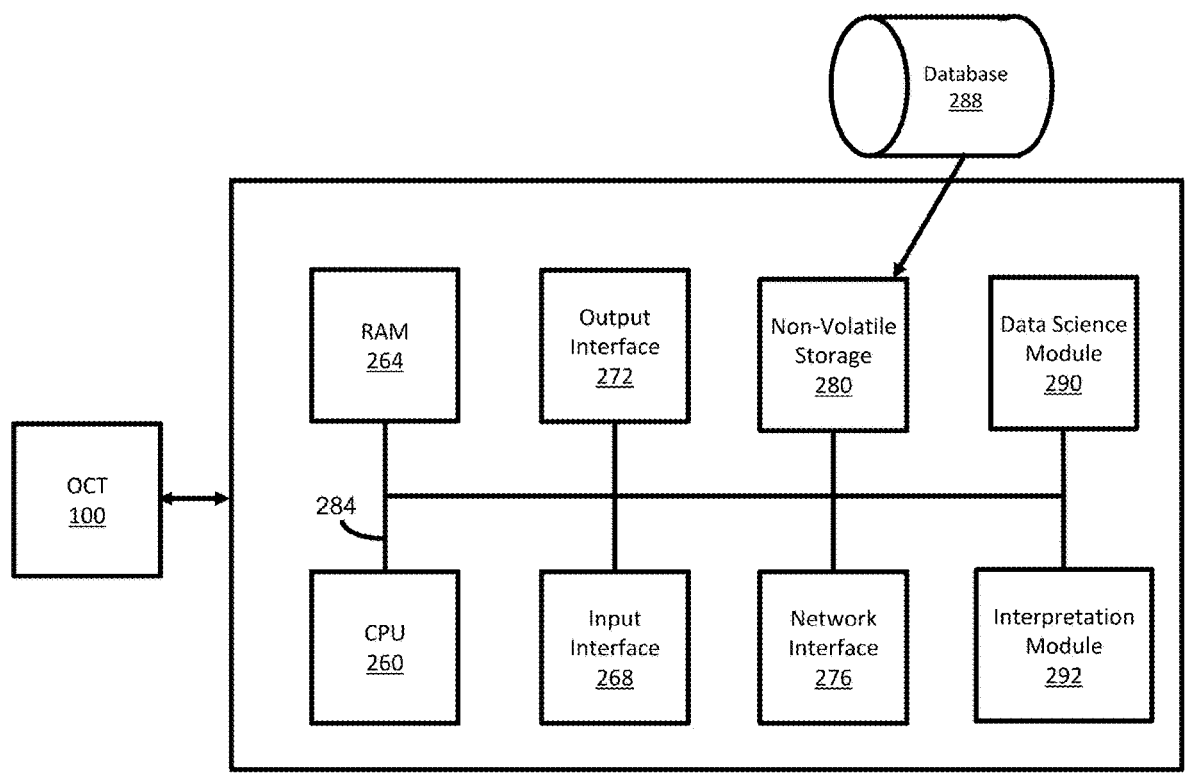
FIG. 2 is a schematic diagram for a neural network system for non-destructive OCT, according to an embodiment.

As shown in FIG. 2, a schematic diagram for a neural network system 200 for non-destructive OCT, according to an embodiment, is shown. As shown, the system 200 has a number of physical and logical components, including a central processing unit ("CPU") 260, random access memory ("RAM") 264, an input interface 268, an output interface 272, a network interface 276, non-volatile storage 280, and a local bus 284 enabling CPU 260 to communicate with the other components. CPU 260 can include one or more processors. RAM 264 provides relatively responsive volatile storage to CPU 260. The input interface 268 enables an administrator to provide input; for example, via a keyboard and mouse. The output interface 272 outputs information to output devices; for example, to a display and speakers. The network interface 276 permits communication with other systems or computing devices; for example, over a local area network or over the Internet. Non-volatile storage 280 stores the operating system and programs, including computer-executable instructions for implementing the OCT system 100 or analyzing data from the OCT system 100, as well as any derivative or related data. In some cases, this data can be stored in a database 288. During operation of the system 200, the operating system, the programs and the data may be retrieved from the non-volatile storage 280 and placed in RAM 264 to facilitate execution. In an embodiment, the CPU 260 can be configured to execute a data science module 290 and an interpretation module 292.

In the present embodiment, the system 200 can be used to detect features associated with the surface and subsurface of an object; and in some cases, categorize such features. In a particular case, such features are defects in the object, due to, for example, various manufacturing-related errors or conditions. In such an example, the system 200 can be used for quality-checking or quality-assurance operations.

The data science module 290 can use machine learning (ML) to transform raw data from the A-scan, B-scan, or C-scan into a descriptor. The descriptor is information associated with a particular defect in the object. The descriptor can then be used by the interpretation module 292 to determine a classifier for the defect. As an example, the data science module 290 can do this detection and classification with auto-encoders as part of a deep belief network. In this sense, ML can be used as part of feature descriptor extraction process, otherwise called "feature learning." In some cases, the data science module 290 can perform the machine learning remotely over a network to an OCT system located elsewhere. The auto-encoder can be trained to learn to reconstruct a representation of the input descriptor to a particular or arbitrary precision; similar to managing quantization error or approximation error of a time series with a set of Fourier/wavelet coefficients.

In further embodiments, instead of, or along with, "feature learning", "feature engineering" can also be undertaken by the data science module 290 to determine appropriate values for discrimination of distinct classes in the OCT data. The data science module 290 can then use ML to provide a posterior probability distribution for class assignment of the object to the class labels. In some cases, "feature engineering" can include input from a user such as a data scientist or computer vision engineer.

In an embodiment, the interpretation module 292 can provide class labels of either "acceptable" or "defective", which it can then provide to the output interface 272. The acceptable label indicates that the object is without defect, or that the number of defects is within an acceptable range in the context of quality control (QC). The defective label indicates that an unacceptable defect has been detected, and in some cases, such defect is of a particular type. In the example where the object is a vehicle part, the defect may have different shapes and dimensions. As an example, the defect may be an unwanted round seed or crater, or the like, on or under the surface of the part. As another example, the defect may have an elongated shape, such as with an unwanted fiber, or the like, on or under the surface of the part. As an example, the acceptable/defective label may be with regards to the size, area, or volume of a defect. In another example, acceptable/defective label may be with regards to the presence of defect between different layers of films applied in an industrial process; for example, in an automotive setting, in an electro-deposition (ED) layer, a colour layer, or a clear layer, where each layer is in the order of tens of microns thick.

In some cases, the interpretation module 292, based on the data science module 290 analysis of the OCT images, can provide further information in the form of feature localization on the object. As an example, the information may be that there is fiber defect at location x=3.4 cm, y=5.6 cm on a vehicle part. Feature localization can also be specified with respect to surface depth, along the z-axis. Depth localization can be particularly advantageous in certain applications; for example, when thin films are being applied to a vehicle part. In this case, for example, after a vehicle part is painted, paint inspection may be required on various layers including an electro-deposition layer, a colour layer, and a clear coat layer. Being able to detect and determine the presence of a defect between any two of these layers is particularly advantageous because it has implications on the amount of re-work that may be required to resolve the imperfection. It can also be advantageous for improvement to a manufacturing process by being able to determine what type of defect is located at what layer; for example, a faulty HVAC system in the manufacturing environment could be responsible for introducing defects between layers. In this regard, being able to localize defect origin to a portion of the manufacturing path is an advantage to reduce future defects and rework.

Figure 3:
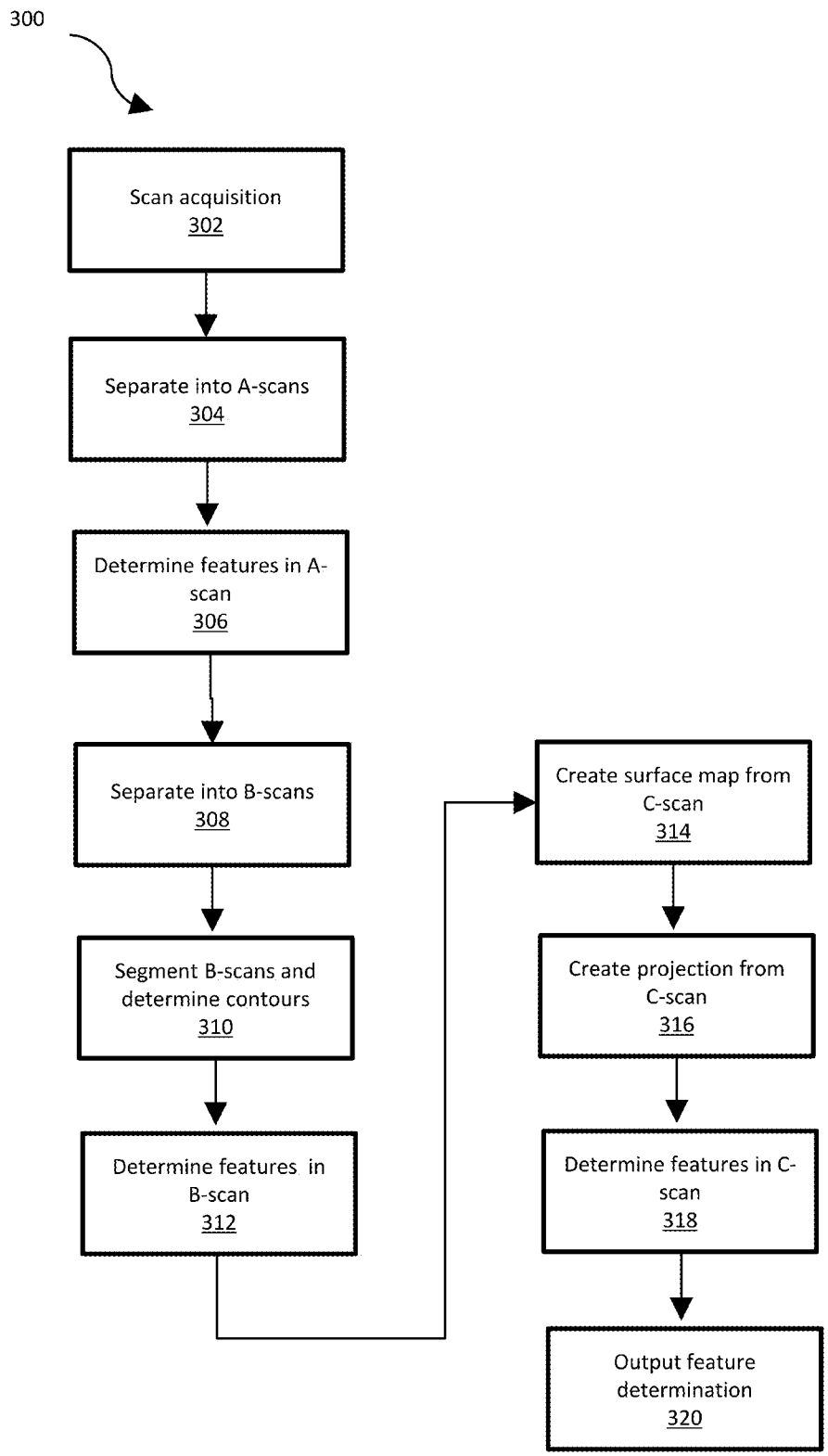
FIG. 3 is a flowchart for a method for implementation of the neural network system for non-destructive OCT, according to an embodiment.

Turning to FIG. 3, a method 300 for implementation of the neural network system 200 for non-destructive OCT, according to an embodiment, is shown. At block 302, acquisition of the scan data is received via the OCT system 100; this can include any of the A-scan, B-scan, or C-scan data. As described above, the scans are received by taking interferometric measurements of the object. The produced C-scan data includes the B-scan data, which itself includes the A-scan data; accordingly, the system 200 can receive the C-scan data from the OCT system 100 and extract the B-scan and A-scan data. In some embodiments, the scan data can be done beforehand and received by the system 200 in bulk.

At block 304, in some cases, each C-scan is separated into its A-scans by the data science module 290. At block 306, each A-scan is successively analysed by the data science module 290 with, for example, a trained Long-Term Short Memory (LSTM) machine learning model in order to detect a feature associated with the object; for example, a defect. For each A-scan, the interpretation module 292 can produce a number between 0 to 1 which indicates the probability of the A-scan being defective, with 0 being representative for defective and 1 being representative of non-defective. In further cases, other scoring or numbering schemes can be used.

Figure 10A:
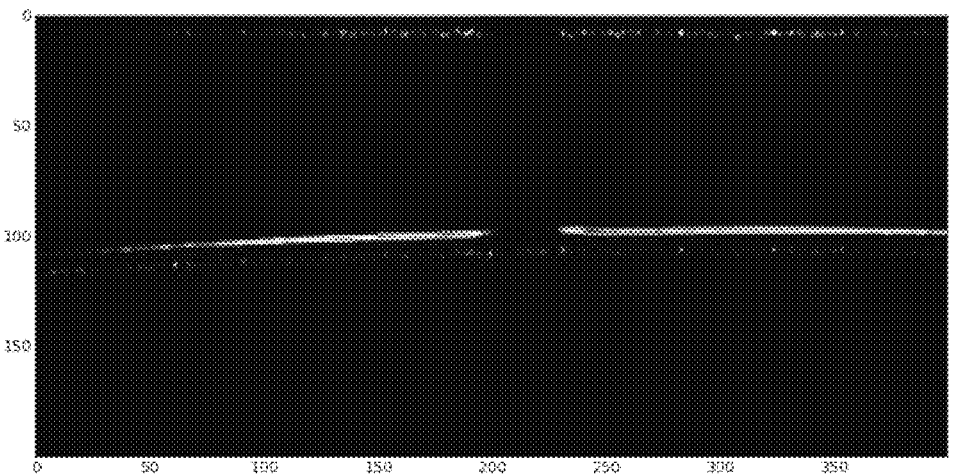
FIG. 10A is an exemplary B-scan in which a defect was detected in a paint layer of a vehicle part using the OCT system of FIG. 1.
Figure 10B:
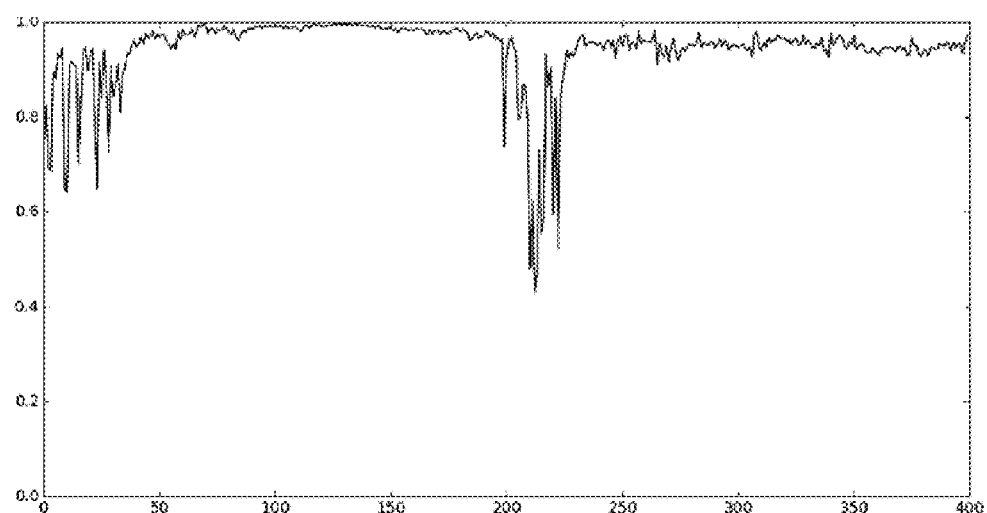
FIG. 10B is a plot of a score produced by the system of FIG. 2 for the exemplary B-scan of FIG. 10A.

As an example, FIG. 10A illustrates an B-scan in which a defect was detected in a paint layer of a vehicle part. As shown, the defect is centered at approximately $225 \times 10^{-2}$ mm along the fast scan axis (x-axis). Correspondingly, FIG. 10B illustrates a plot of a score produced by the interpretation module 292, between 0 and 1, representing a determined possibility that a defect is present in the exemplary B-scan of FIG. 10A.

At block 308, in some cases, the data science module 290 separates each C-scan into B-scans, or into A-scans, if it was not done so at block 304, to get the B-scans.

At block 310, each B-scan is segmented by the data science module 290 such that contours in the scan can be detected. The segmentation to determine contours or thresholds can use, for example, Canny edge detection, Otsu clustering-based image thresholding, Integral Image Thresholding such as the Bradley-Roth adaptive thresholding, or the like.

At block 312, based on the continuity of the determined contours and/or thresholds, the data science module 290 can use a trained Long-Term Short Memory (LSTM) machine learning model in order to detect a feature associated with the object; for example, a defect.

Figure 11A:
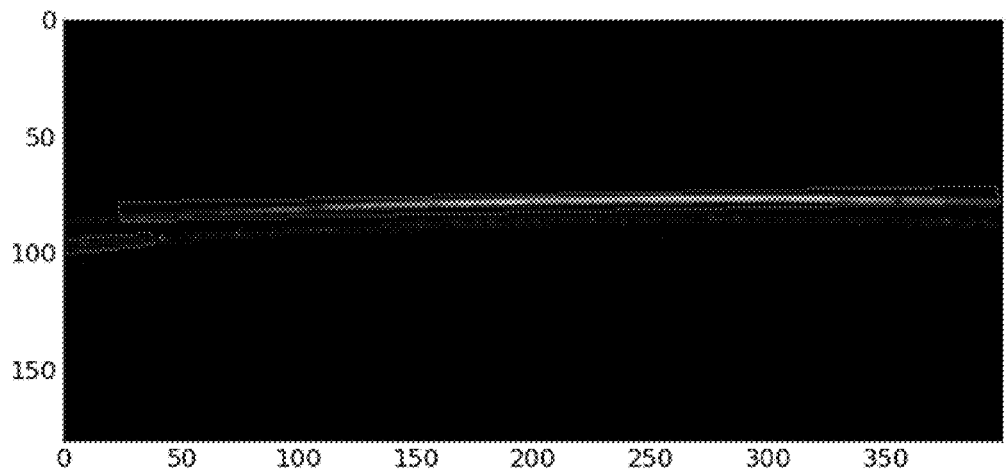
FIG. 11A is an exemplary B-scan using the OCT system of FIG. 1, in which the system of FIG. 2 determined there are no features present.
Figure 11B:
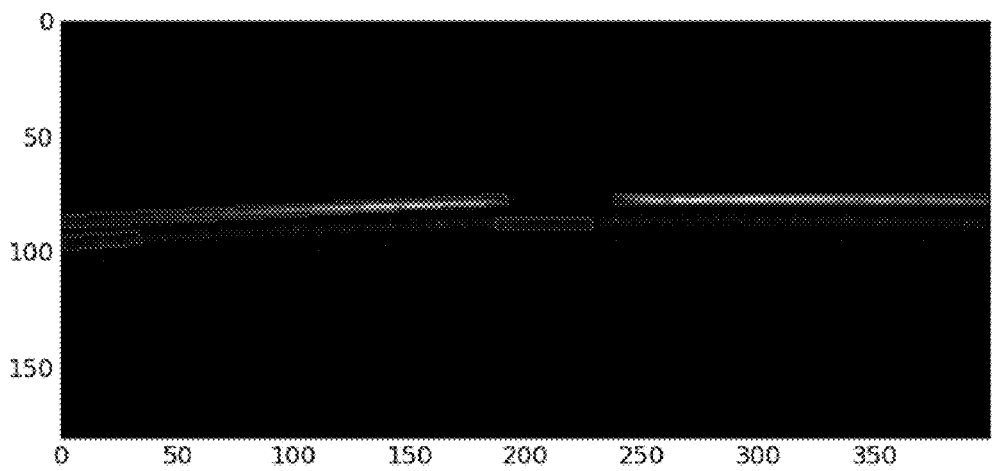
FIG. 11B is an exemplary B-scan using the OCT system of FIG. 1, in which the system of FIG. 2 determined there are features present.

As an example, FIG. 11A illustrates a B-scan in which contours are outlined. In this case, the data science module 290 determined that there was no defect detected on the object. FIG. 11B also illustrates a B-scan in which contours are outlined. In this case, the data science module 290 determined that there was a defect detected on the object. The interpretation module 292 can then determine the coordinates and size of the feature from the determination of the feature's contours. In this example, the interpretation module 292 determined that this defect occurs between approximately 175 and 240 along the x-axis.

In some cases, in order to inspect the C-scan for features, the C-scan can be converted to a two-dimensional image using two approaches, a surface map and a projection. At block 314, the data science module 290 extracts a surface map from the C-scan. To extract the surface-map, the data science module 290 finds a region of interest (ROI) from the B-scan image via segmentation and thresholding, as described above. Once the ROI is determined, image segmentation techniques can be used by the data science module 290 to segment the structure or layers of the object into B-Scans. In this example, image segmentation is accomplished based on a graph cuts approach. In further examples, image segmentation is accomplished based on a graph search approach. The data science module 290 can use the detected layer to create surface maps, whereby each B-scan can be mapped to a line which represents the distance from the surface of the B-scan.

Figure 12:
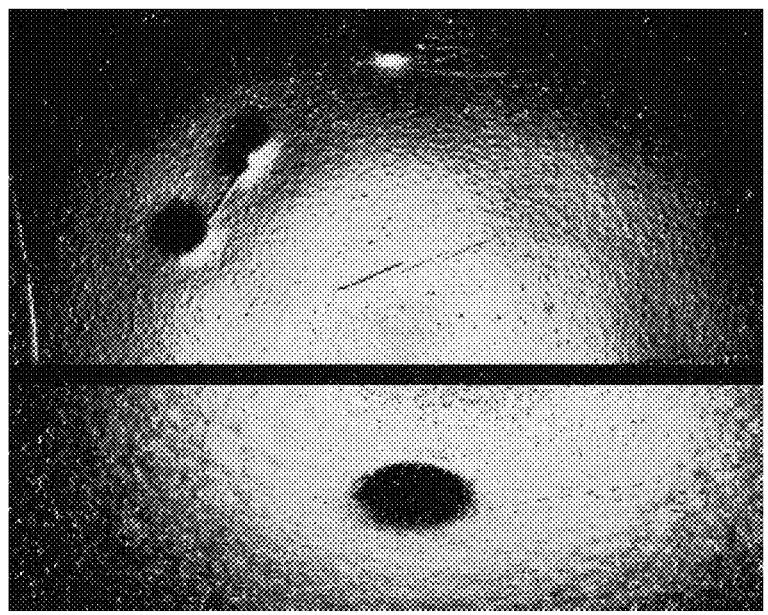
FIG. 12 is an exemplary surface map generated by the system of FIG. 2.

As an example, FIG. 12 illustrates a surface map determined by the data science module 290 as described above.

At block 316, the data science module 290 determines a projection of the C-scan. By determining an integral along the Z-axis, the data science module 290 can determine the projection. Whereby each A-scan can be mapped onto one point that is the integral of the intensities along that A-scan axis. Then each of such mapped points can be combined in the C-scan to construct a two-dimensional projection map. In other words, once each A-scan of a given B-scan is mapped to a point as described above, the whole B-scan can be mapped to a line on the two-dimensional projection of the C-scan. Since the peaks in an A-scan correspond to the layers of the object in the z-direction, the averaged or summed intensity of each A-scan point on the projected C-scan map can be used to visualize and detect defects or abnormalities in the C-scan.

At block 318, once the two-dimensional projections and surface maps are created, the data science module 290 can use a Gabor wavelet filter to detect features on the object, such as defects. In some cases, 2D Gabor wavelet filters can be used to extract textural features in multiple orientations and multiple scales on images. Gabor filters generally analyze specific frequency content on a specific direction. Combined with wavelet transformation, Gabor wavelets have both multi-resolution and multi-orientation properties and are beneficial for measuring local spatial frequencies. These features extracted from C-scan surface maps or projection maps can then be used as input to further machine learning techniques, depending on the application, to detect or segment defects. In some cases, once the location of defects is detected, the projection and/or surface map can be cropped around the area of defect. Once the location is determined, the data science module 290 can determine the type of defect by using a Convolutional Neural Network (CNN). The interpretation module 292 can then determine the coordinates and size of the feature.

At block 320, the determinations of the data science module 290 and the interpretation module 292 are outputted via the output interface 272 in any suitable format; for example, images, graphs, alerts, textual information, or the like. In further embodiments, the determinations can be provided to other systems or machinery.

Figure 13:
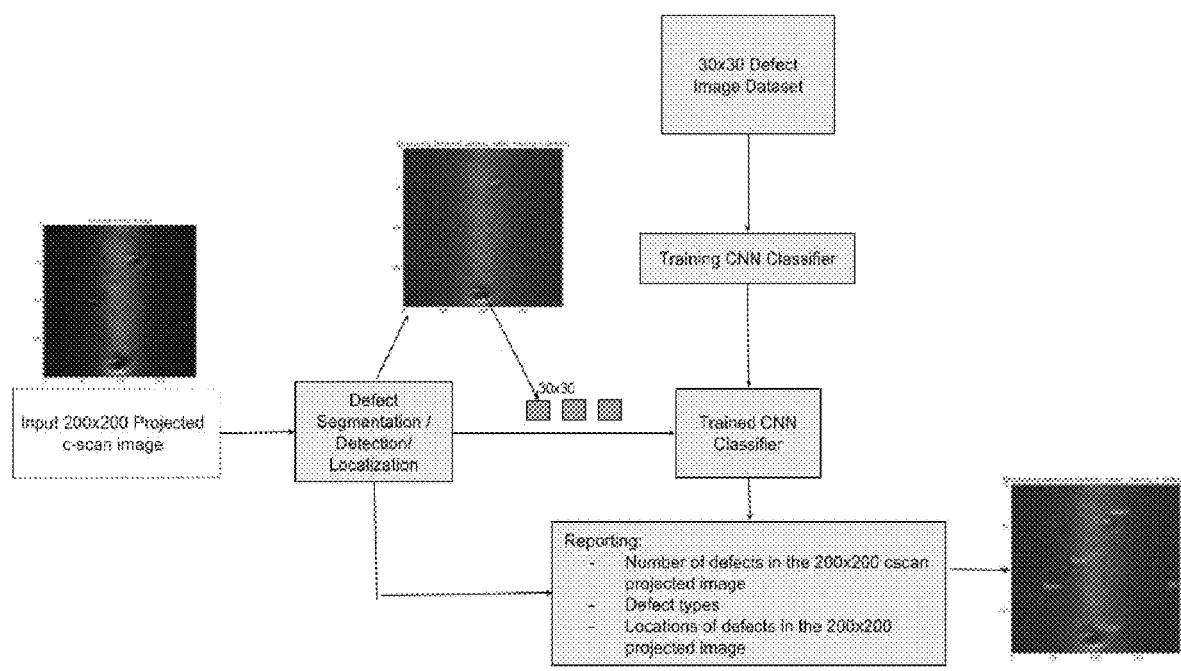
FIG. 13 is an exemplary diagrammatic overview of the method of FIG. 3.

FIG. 13 illustrates an exemplary diagrammatic overview, including sample scans, of the method 300 for implementation of the neural network system 200 for non-destructive OCT.

The machine-learning based analysis of the data science module 290 may be implemented by providing input data to the neural network, such as a feed-forward neural network, for generating at least one output. The neural networks described herein may have a plurality of processing nodes, including a multi-variable input layer having a plurality of input nodes, at least one hidden layer of nodes, and an output layer having at least one output node. During operation of a neural network, each of the nodes in the hidden layer applies a function and a weight to any input arriving at that node (from the input layer or from another layer of the hidden layer), and the node may provide an output to other nodes (of the hidden layer or to the output layer). The neural network may be configured to perform a regression analysis providing a continuous output, or a classification analysis to classify data. The neural networks may be trained using supervised or unsupervised learning techniques, as described above. According to a supervised learning technique, a training dataset is provided at the input layer in conjunction with a set of known output values at the output layer. During a training stage, the neural network may process the training dataset. It is intended that the neural network learn how to provide an output for new input data by generalizing the information it learns in the training stage from the training data. Training may be affected by back-propagating error to determine weights of the nodes of the hidden layers to minimize the error. The training dataset, and the other data described herein, can be stored in the database 288 or otherwise accessible to the system 200. Once trained, or optionally during training, test data can be provided to the neural network to provide an output. A neural network may thus cross-correlate inputs provided to the input layer in order to provide at least one output at the output layer. Preferably, the output provided by a neural network in each embodiment will be close to a desired output for a given input, such that the neural network satisfactorily processes the input data.

In some cases, the training dataset can be imported in bulk from a historical database of OCT scans and labels, or feature determinations, associated with such scans.

In further cases, the system 200 can first operate in a 'training mode'. In such training mode, OCT scans are acquired by the system 200. Feature engineering can be manually determined, or determined automatically with manual oversight, and includes: shape detection or characterization; pixel intensity determinations such as histogram equalization, mathematical morphology, local binary patterns; wavelets, thresholding, or the like; or bilateral filtering, total variation filtering, or the like.

Figure 4:
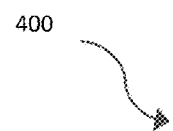
FIG. 4 is an exemplary image captured using the OCT system of FIG. 1.
Figure 4:
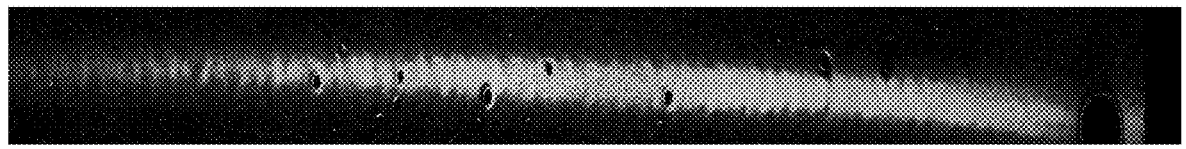

FIG. 4 illustrates an exemplary image 400 captured using the OCT system 100 to form a top-level surface view of an object.

Figure 5A:
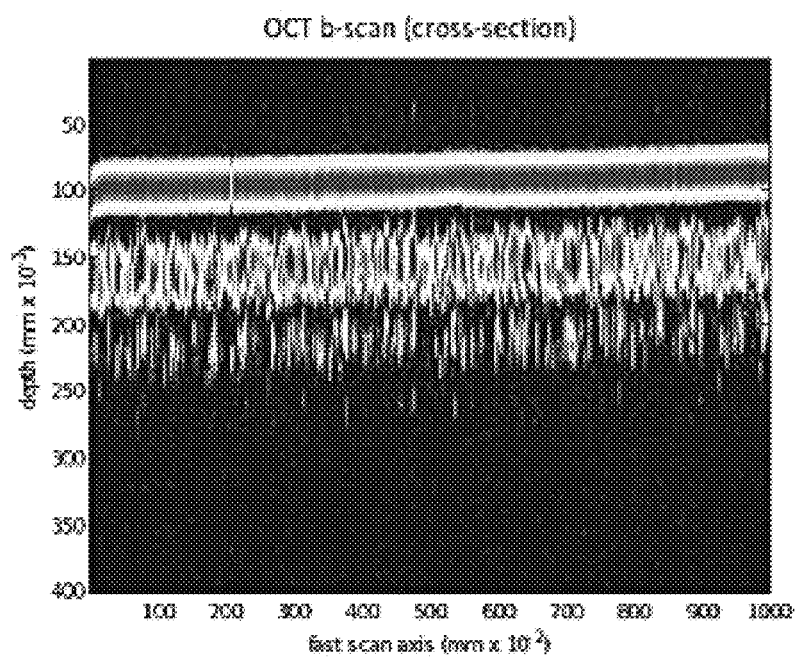
FIG. 5A is an exemplary B-scan of an object without problematic defects or features using the OCT system of FIG. 1.
Figure 5B:
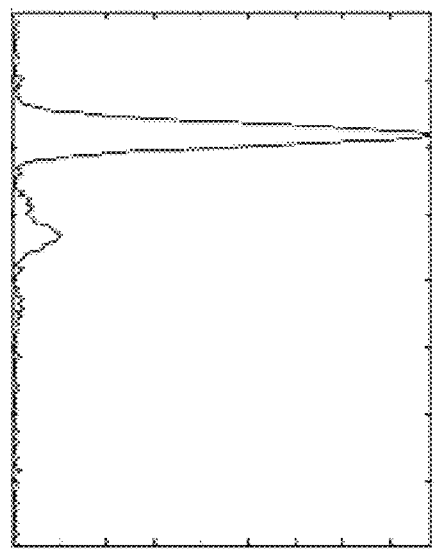
FIG. 5B is an exemplary A-scan of the object of FIG. 5A using the OCT system of FIG. 1.

FIG. 5A illustrates an exemplary B-scan (cross-section) of an object without problematic defects or features (i.e., a 'clean' surface) using the OCT system 100. FIG. 5B illustrates an exemplary A-scan from the center of the B-scan of FIG. 5A using the OCT system 100.

Figure 6:
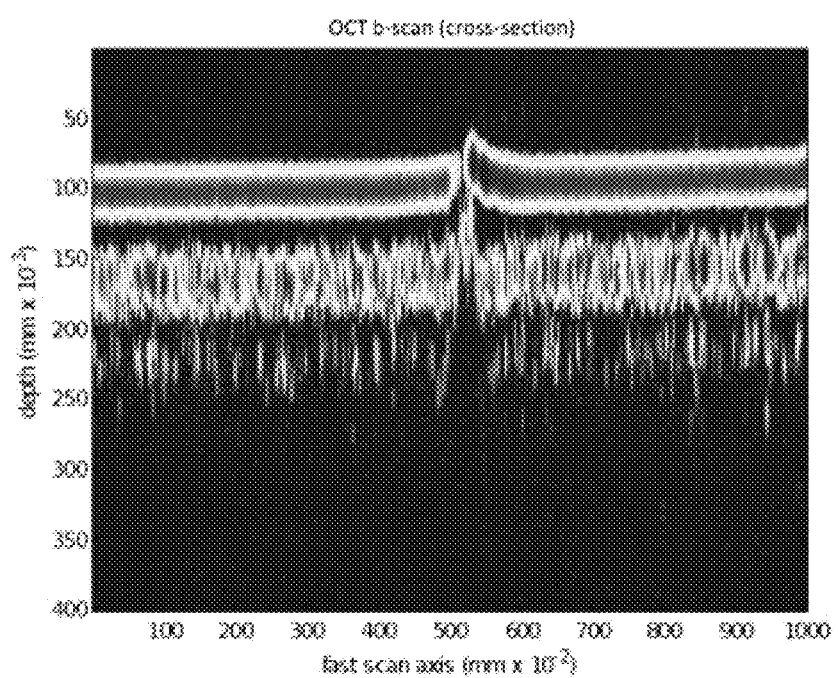
FIG. 6 is an exemplary B-scan of an object with problematic defects or features using the OCT system of FIG. 1.

FIG. 6 illustrates an exemplary B-scan (cross-section) of an object with a problematic defects or feature present using the OCT system 100. In this case, as shown, there was a subsurface seed detected, centered at approximately 500 along the x-axis.

Figure 7:
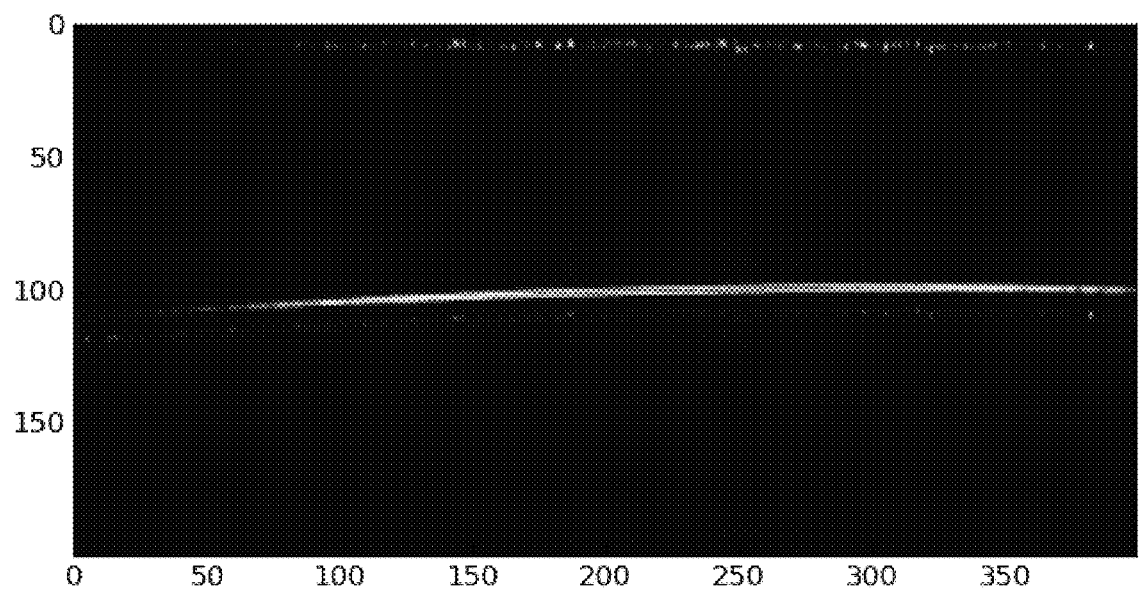
FIG. 7 is an exemplary B-scan of an object for determining whether there are defects using the OCT system of FIG. 1.
Figure 8:
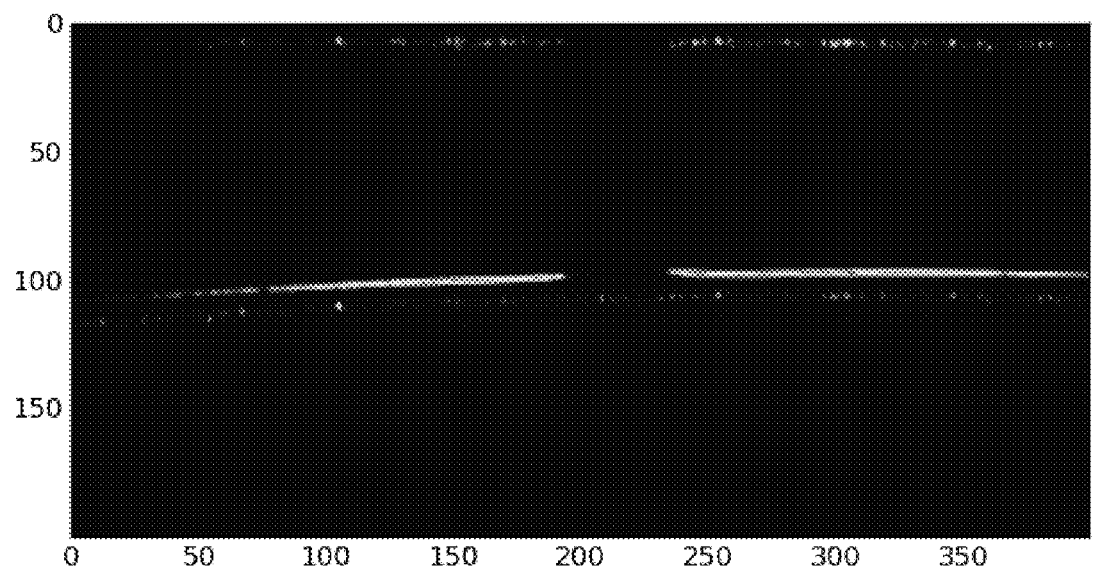
FIG. 8 is an exemplary B-scan of an object, showing a defect, using the OCT system of FIG. 1.

FIG. 7 illustrates an exemplary B-scan of a vehicle part for determining whether there are painting defects using the OCT system 100. In this case, there was no detects from the A-scan. FIG. 8 illustrates an exemplary B-scan of a vehicle part for determining whether there are painting defects using the OCT system 100. In this case, as shown, there was a defect in the paint layer detected, centered at approximately 225 along the x-axis.

Figure 9A:
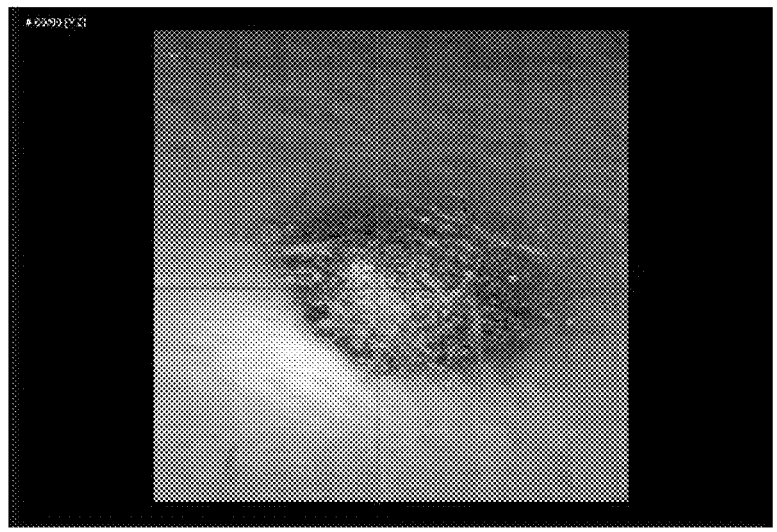
FIGS. 9A and 9B are exemplary C-scans, at respectively different angles of perspective, of a vehicle part using the OCT system of FIG. 1.
Figure 9B:
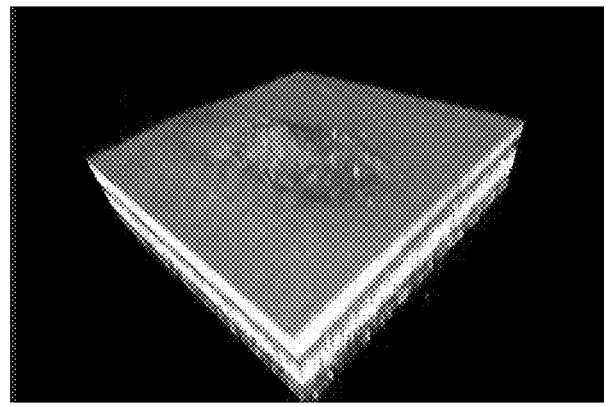

FIGS. 9A and 9B illustrate, at respectively different angles of perspective, an exemplary C-scan of a vehicle part using the OCT system 100. In this case, a seed was detected as a defect in the painting of a vehicle part.

In exemplary embodiments described herein, the data science module 290 can perform the detection by employing, at least in part, an LSTM machine learning approach. The LSTM neural network allows the system 200 to quickly and efficiently perform group feature selections and classifications.

Figure 14:
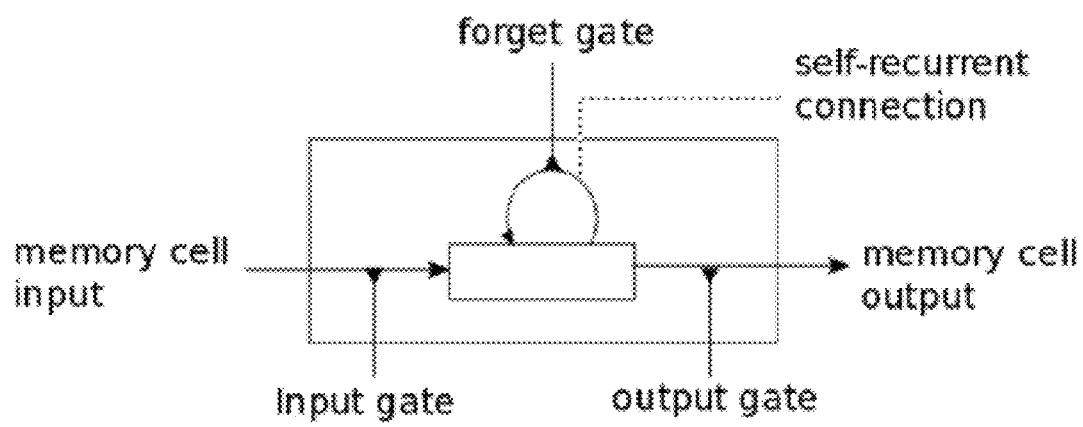
FIG. 14 is diagram of a memory cell.

The LSTM neural network is a category of neural network model specified for sequential data analysis and prediction. The LSTM neural network comprises at least three layers of cells. The first layer is an input layer, which accepts the input data. The second (and perhaps additional) layer is a hidden layer, which is composed of memory cells (see FIG. 14). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

Layers of the memory cells can be updated at every time step, based on an input array (the OCT scan data). Using weight matrices and bias vectors, the values at the input gate of the memory cell and the candidate values for the states of the memory cells at the time step can be determined. Then, the value for activation of the memory cells' forget gates at the time step can be determined. Given the value of the input gate activation, the forget gate activation and the candidate state value, the memory cells' new state at the time step can be determined. With the new state of the memory cells, the value of their output gates can be determined and, subsequently, their outputs.

Based on the model of memory cells, at each time step, the output of the memory cells can be determined. Thus, from an input sequence, the memory cells in the LSTM layer will produce a representation sequence for their output. Generally, the goal is to classify the sequence into different conditions. The Logistic Regression output layer generates the probability of each condition based on the representation sequence from the LSTM hidden layer. The vector of the probabilities at a particular time step can be determined based on a weight matrix from the hidden layer to the output layer, and a bias vector of the output layer. The condition with the maximum accumulated probability will be the predicted outcome of this sequence.

In exemplary embodiments described herein, the data science module 290 can perform the detection by employing, at least in part, a CNN machine learning approach.

CNN machine learning models are generally a neural network that is comprised of neurons that have learnable weights and biases. In a particular case, CNN models are beneficial when directed to extracting information from images. Due to the specificity of being directed to images, CNN models are advantageous because such models allow for a forward function that is more efficient to implement and reduces the amount of parameters in the network. Accordingly, the layers of a CNN model generally have three-dimensions of neurons called width, height, and depth; whereby depth refers to an activation volume. The capacity of CNN models can be controlled by varying their depth and breadth, such that they can make strong and relatively correct assumptions about the nature of images, such as stationarity of statistics and locality of pixel dependencies.

Typically, the input for the CNN model includes the raw pixel values of the input images. A convolutional layer is used to determine the output of neurons that are connected to local regions in the input. Each layer uses a dot product between their weights and a small region they are connected to in the input volume. A rectified linear units layer applies an element by element activation function, $f(x)=\max(0, x)$, to all of the values in the input volume. This layer increases the nonlinear properties of the model and the overall network without affecting the receptive fields of the convolutional layer. A pooling layer performs a down-sampling operation along the spatial dimensions. This layer applies a filter to the input volume and determines the maximum number in every subregion that the filter convolves around. As typically of a neural network, each output of a neuron is connected to other neurons with back-propagation.

While the method 300 and system 200 are described as using certain machine-learning approaches, specifically LSTM and CNN, it is appreciated that, in some cases, other suitable machine learning approaches may be used where appropriate.

In further embodiments, machine learning can also be used by the data science module 290 to detect and compensate for data acquisition errors at the A-scan, B-scan and C-scan levels.

The embodiments described herein include various intended advantages. As an example, quick determination of features, such as defects, on a surface or subsurface of an object, without necessitating costly and timely manual oversight or analysis of the truth of such feature. Furthermore, information regarding such feature can be extracted in order to provide information on how to avoid or alter the features in the future.

While the above-described embodiments are primarily directed to detecting defects, those skilled in the art will appreciate that the same approach can be used for detecting other features of objects and used in various applications of OCT.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

The invention claimed is:

1. A system for non-destructive optical coherence tomography (OCT), the system comprising:
an input interface for receiving OCT data of an object;
a processing unit executable to detect one or more features on a surface or subsurface of the object via a data science module, the data science module configured to:
using a trained A-scan neural network, analyze each of a plurality of A-scans from the OCT data to detect the presence of an A-scan feature associated with the object;
segment each of a plurality of B-scans from the OCT data to determine thresholds associated with the object;
using a trained B-scan neural network, analyze each segmented B-scan to detect the presence of a B-scan feature associated with the object;
convert a C-scan from the OCT data to one or more two-dimensional representations; and
using a trained C-scan neural network, detect the presence of a C-scan feature associated with the object; and
an output interface for outputting the analyses and detections of the data science module.

2. The system of claim 1, wherein the OCT data comprises at least one C-scan, and wherein the data science module is further configured to separate the at least one C-scan into the plurality of A-scans.

3. The system of claim 2, wherein the data science module is further configured to separate the at least one C-scan into the plurality of B-scans.

4. The system of claim 1, wherein each of the plurality of A-scans are analyzed successively and each of the plurality of B-scans are analyzed successively.

5. The system of claim 1, wherein the training data for the A-scan neural network, the B-scan neural network, and the C-scan neural network comprises historical data of previous OCT scans and associated features.

6. The system of claim 1, wherein the training data for the A-scan neural network, the B-scan neural network, and the C-scan neural network is received by initially operating in a training mode where features associated with the OCT data are determined with manual input via the input interface.

7. The system of claim 1, wherein the A-scan neural network uses a trained Long-Term Short Memory (LSTM) machine learning model, the B-scan neural network uses another trained Long-Term Short Memory (LSTM) machine learning model, and the C-scan neural network uses a Convolutional Neural Network (CNN).

8. The system of claim 7, wherein the A-scan neural network outputs a score representing a probability for the detection of the presence of the A-scan feature.

9. The system of claim 1, wherein the segmenting of each B-scan comprises determining thresholds using at least one of Canny edge detection, Otsu clustering-based image thresholding, and Integral Image Thresholding.

10. The system of claim 1, wherein the converting of the C-scan from the OCT data to one or more two-dimensional representations comprises extracting a surface map from the C-scan and determining a projection of the C-scan.

11. The system of claim 10, wherein the extracting of the surface map comprises determining regions-of-interest (ROI) from the segmented B-scans, using image segmentation techniques to segment layers of the object into B-Scans, and using the layers to create surface maps by mapping each B-scan to a line that represents a distance from a surface of the B-scan.

12. The system of claim 10, wherein the determining of the projection comprises mapping each A-scan onto a point that is an average or sum of the intensities along an A-scan axis and combining each of the mapped points in the C-scan to construct a two-dimensional projection map.

13. The system of claim 10, wherein detecting the presence of the C-scan feature comprises using a Gabor filter with the projection and surface map.

14. The system of claim 1, the processing unit further executable to determine coordinates, size, or both, of at least one of the A-scan feature, B-scan feature, and C-scan feature via an interpretation module.

15. A computer-implemented method for non-destructive optical coherence tomography (OCT), the method comprising:
  receiving OCT data of an object;
  detecting one or more features on a surface or subsurface of the object by:
    using a trained A-scan neural network, analyzing each of a plurality of A-scans from the OCT data to detect the presence of an A-scan feature associated with the object;
    segmenting each of a plurality of B-scans from the OCT data to determine thresholds associated with the object;
    using a trained B-scan neural network, analyzing each segmented B-scan to detect the presence of a B-scan feature associated with the object;
    converting a C-scan from the OCT data to one or more two-dimensional representations; and
    using a trained C-scan neural network, detecting the presence of a C-scan feature associated with the object; and
  outputting the analyses and detections.

16. The method of claim 15, wherein the OCT data comprises at least one C-scan, the method further comprising separating each C-scan into the plurality of B-scans and separating the B-scans into the plurality of A-scans.

17. The method of claim 15, wherein converting of the C-scan from the OCT data to one or more two-dimensional representations comprises extracting a surface map from the C-scan and determining a projection of the C-scan.

18. The method of claim 17, wherein extracting of the surface map comprises determining regions-of-interest (ROI) from the segmented B-scans, using image segmentation techniques to segment layers of the object into B-Scans, and using the layers to create surface maps by mapping each B-scan to a line that represents a distance from a surface of the B-scan.

19. The method of claim 17, wherein determining the projection comprises mapping each A-scan onto a point that is an average or sum of the intensities along an A-scan axis and combining each of the mapped points in the C-scan to construct a two-dimensional projection map.

20. The method of claim 17, wherein detecting the presence of the C-scan feature comprises using a Gabor filter with the projection and surface map.

\* \* \* \* \*